(12) United States Patent
Chu et al.

(10) Patent No.: US 11,534,220 B2
(45) Date of Patent: Dec. 27, 2022

(54) NEGATIVE PRESSURE GUIDED BONE CEMENT INJECTION SYSTEM

(71) Applicant: NATIONAL YANG-MING UNIVERSITY, Taipei (TW)

(72) Inventors: Woei-Chyn Chu, Taipei (TW); Yin-Jiun Tseng, Taipei (TW); William Chu, Taipei (TW)

(73) Assignee: NATIONAL YANG-MING UNIVERSITY, Taipei (TW)

(*) Notice: Subject to any disclaimer, the term of this patent is extended or adjusted under 35 U.S.C. 154(b) by 389 days.

(21) Appl. No.: 16/473,428

(22) PCT Filed: Dec. 8, 2017

(86) PCT No.: PCT/CN2017/115303
§ 371 (c)(1),
(2) Date: Nov. 15, 2019

(87) PCT Pub. No.: WO2018/103742
PCT Pub. Date: Jun. 14, 2018

(65) Prior Publication Data
US 2020/0383715 A1 Dec. 10, 2020

Related U.S. Application Data

(60) Provisional application No. 62/431,540, filed on Dec. 8, 2016.

(51) Int. Cl.
*A61B 17/88* (2006.01)
(52) U.S. Cl.
CPC ...... *A61B 17/8805* (2013.01); *A61B 17/8811* (2013.01); *A61B 17/8822* (2013.01); *A61B 2017/8844* (2013.01)

(58) Field of Classification Search
CPC ............ A61B 17/8802; A61B 17/8805; A61B 17/8816; A61B 17/8819; A61B 17/8833; A61B 17/885; A61B 17/8822; A61B 17/8811; A61B 17/1757; A61B 2017/8844
See application file for complete search history.

(56) References Cited

U.S. PATENT DOCUMENTS

| | | | | |
|---|---|---|---|---|
| 2001/0049531 A1* | 12/2001 | Reiley | ............... | A61B 17/8811 606/93 |
| 2006/0036241 A1* | 2/2006 | Siegal | ............... | A61B 17/1757 606/279 |
| 2007/0118144 A1* | 5/2007 | Truckai | ............. | A61B 17/8836 606/93 |
| 2007/0161943 A1* | 7/2007 | Lidgren | ............. | A61B 17/8822 604/19 |

* cited by examiner

*Primary Examiner* — Amy R Sipp
(74) *Attorney, Agent, or Firm* — WPAT, PC

(57) ABSTRACT

The present invention provides a negative pressure guided bone cement injection system comprising a negative pressure system, comprising a negative pressure introduction device, a pushing system for implant bone cement to the target area, a control system for regulating the negative pressure system and the pushing system, and at least one sensing device disposed at any position of the negative pressure system, which can sense at least one environmental parameter for observing the physiological condition of a patient's spinal vertebral body can be monitored immediately, and the result is actively or passively sent back to the system or the operator for adjusting the injection parameters.

15 Claims, 11 Drawing Sheets

|  | Excellent | Good | Poor | Failed | Leakage of bone cement | | Leakage of bone cement (intervertebral disc) | Leakage of bone cement (vein) | Leakage of bone cement (posterior epidural) | Neural system complications |
|---|---|---|---|---|---|---|---|---|---|---|
|  |  |  |  |  | Leakage to spinal cord | | | | | |
| vertebroplasty with one-way bone cement injection group (Condition 1) | 6/26 (23%) | 5/26 (19%) | 8/26 (31%) | 7/26 (27%) | 14/26 (54%) Leakage | 10 (38%) | 5 (19%) | 3 (12%) | 7 (27%) | 2 (8%) |
| vesselplasty with one-way bone cement injection group (Condition 2) | 12/36 (33%) | 7/36 (20%) | 9/36 (25%) | 8/36 (22%) | 19/36 (53%) Leakage | 11 (31%) | 7 (20%) | 5 (14%) | 2 (6%) | 0 |
| vertebroplasty with two-way bone cement injection group (Condition 3) | 13/25 (52%) | 5/25 (20%) | 4/25 (16%) | 3/25 (12%) | 14/25 (56%) Leakage | 8 (32%) | 4 (16%) | 2 (8%) | 2 (8%) | 0 |
| vesselplasty with two-way bone cement injection group (Condition 4) | 24/41 (59%) | 9/41 (22%) | 5/41 (12%) | 3/41 (7%) | 13/41 (32%) Leakage | 9 (22%) | 3 (7%) | 1 (3%) | 1 (3%) | 0 |
| vertebroplasty with two-way bone cement injection with negative pressure guidance group (Condition 5) | 38/50 (76%) | 7/50 (14%) | 3/50 (6%) | 2/50 (4%) | 6/50 (12%) Leakage | 4 (8%) | 2 (4%) | 0 | 0 | 0 |
| vesselplasty with two-way bone cement injection with negative pressure guidance group (Condition 6) | 63/78 (81%) | 10/78 (13%) | 3/78 (4%) | 2/78 (3%) | 7/78 (9%) Leakage | 5 (6%) | 2 (3%) | 0 | 0 | 0 |

Fig. 10

NEGATIVE PRESSURE GUIDED BONE CEMENT INJECTION SYSTEM

CROSS-REFERENCE TO RELATED APPLICATION

Background of the Invention

Technical Field of the Invention

The present invention relates to a bone cement injection system. More particularly, the present invention relates to a negative pressure guided bone cement injection system.

Background

Since the end of the twentieth century when bone cement was used to treat the pain of spinal hemangioma, the importance of the bone fillers for the use of orthopedics has started to increase. Especially, a treatment using bone fillers to support spinal bone and format a vertebral body can replace the traditional nerve decompression surgery or spinal fixation surgery to help spinal cord avoiding compression. The treatment procedure has been widely used as one of the effective methods to enhance the stability of the spine in the treatment of compression fractures caused by various primary and secondary osteoporosis. Furthermore, the treatment can be further applied to general fractures caused by aging.

The minimally invasive surgery for vertebral body formation is performed in the vertebral body by percutaneous puncture by filling the damaged vertebral body with the poly-methyl methacrylate (PMMA) or other bone filling material to enhance the strength of the vertebral body and the stability of the spine and reduce the chronic pain caused by the damage of the vertebral body. Therefore, in order to implant the bone filling material into the damaged vertebral body smoothly, the equipment used to implant the bone filling material is very important. The equipment's stability of the injection rate, the convenience of applying force, the characteristic of reuse and the adaptability of other equipment are inseparable from the difficulty of operation and indirectly affect the outcome of the surgery as well.

Nowadays, most of the repair material injection devices are using syringe as the main body, meaning that the repairing material is placed in the injection syringe with a special injection needle at the injection end, and then push the syringe like the general injection way to inject the repairing material into the target bone through the specially designed injection needle. However, during this injection way, the resistance to push the piston will get stronger because that the repairing material will become more and more solidified during the injection process. In this case, not only the injection of the repairing material is difficult to process, but also the rate of injection is getting slower. And in the process of overcoming the slowing down of the injection rate, the operator may force excessive injection pressure and cause the leakage of repairing material to other areas. Generally, the whole procedure is inconvenient.

The biggest challenge in the operation equipment of bone cement injection is that the change in viscosity of bone cement getting coagulating causes the clogging problem, or the injection port is not able to continuously inject because of the clogging in the vertebral body of the patient's spine. It increases the difficulty in operation. Therefore, there are several improvements like modifying the injection way or a temperature control device to slow down the bone cement solidification. However, there is still no consistent and effective improvement way that can overcome the clogging in the vertebral body of the patient's spine to allow the operation equipment of bone cement to continuously inject under the circumstances.

On the other hand, in order to improve the bone cement overflow problem during the injection process, there is an article (Young, S T., et al., Injury, 2013. 44(6): p. 813-818) disclosing a safer and more effective bone cement injection method applying a constant continuous negative pressure to the opposite side of the vertebral body when injecting bone cement to reduce the leakage rate of the bone cement during the injection process. However, this injection method can only help doctor pre-controlling the presupposition of the potential clogging or overflow of bone cement based on the doctor's experience. When the actual physiological condition inside the vertebral body is not as expected, this method cannot respond precisely to the actual situation. If the pressure inside the vertebral body gets too high, it might lead to microvascular rupture or increasement in blood loss. Oppositely, if the pressure gets too low, it might cause a poor bone cement guiding effect and increase the risk of the leakage into the cavity or vein, causing complications of spinal cord compression or pulmonary embolism.

Therefore, how to provide a good bone cement injection system that is capable of overcoming the risks which might occur during the injection and monitoring the physiological condition of the patient's spinal vertebral body immediately to send a feedback to the system for correcting a parameter actively or to the operate for receiving parameter correction passively to avoid the complications of the surgical procedure, which has become an urgent problem in this and any relevant industries.

SUMMARY OF INVENTION

Accordingly, the present invention provides a negative pressure guided bone cement injection system, and through which, the physiological condition of a patient's spinal vertebral body can be monitored immediately, and the result is actively or passively sent back to the system or the operator for adjusting the injection parameters.

The present invention provides a negative pressure guided bone cement injection system, and through which, the fluidity of the bone cement can be controlled by adjusting the ratio of the bone cement materials immediately, as one of the injection conditions, based on the physiological condition of a patient's spinal vertebral body.

The present invention provides a negative pressure guided bone cement injection system, and through which, an introduction opening of a negative pressure device and an introduction opening of a bone cement implantation system of a pushing system are disposed oppositely to each other to elevate the efficiency of the negative pressure system.

The present invention discloses a negative pressure guided bone cement injection system, comprising a negative pressure system, a pushing system, a control system and at least one sensing device, wherein the negative pressure system comprises a negative pressure introduction device having one side connected to a negative pressure source, and a cavity therein, wherein the negative pressure source provides a negative pressure to another side of the negative pressure introduction device via the cavity; wherein the pushing system comprises a pushing pump and a bone cement implantation system, wherein the pushing pump pushes a bone cement material in the bone cement implantation system for delivery, and the at least one sensing device is disposed at any position of the negative pressure system, and is electrically connected to the control system for sensing at least one environmental parameter, and then sends the at least one environmental parameter to the control system.

In one embodiment of the present invention, the negative pressure system further comprises a negative pressure supply device, providing a negative pressure, and a first adjusting device connected to the negative pressure supply device for adjusting the output of the negative pressure supply device and electrically connected to the control system for adjusting the negative pressure supply device by the control from the control system.

In one embodiment of the present invention, the negative pressure supply device is a negative pressure pump or a medical negative pressure socket.

In one embodiment of the present invention, the pushing system further comprises a second adjusting device electrically connected to the pushing pump and the control system, the second adjusting device configured for being controlled by the control system to regulate the pushing strength of the pushing pump on the bone cement material.

In one embodiment of the present invention, the first adjusting device and the second adjusting device are a flow regulating valve, a current regulator or a voltage regulator.

In another embodiment of the present invention, the at least one sensing device is disposed on the negative pressure system and the pushing system for sensing the at least one environmental parameter of the negative pressure system and the pushing system and sending the at least parameter to the control system to adjust and control the negative pressure guided bone cement injection system.

In one embodiment of the present invention, the at least one environmental parameter is a viscosity of the bone cement material, a flow rate of the bone cement, a density of the bone cement material, a bone density, a negative pressure in the negative pressure introduction device, a negative pressure in the negative pressure system or a negative pressure in a target region.

In another embodiment of the present invention, the at least one sensing device senses the at least one environmental parameter and then sends the at least one environmental parameter to the control system for calculating and generating an operation result. And the strength of the negative pressure of the negative pressure system and/or the pushing strength of the pushing system is/are regulated based on the operation result.

In one embodiment of the present invention, the negative pressure introduction device is a first needle tube, comprising a hollow first needle body and a first tube body. The first needle body has one side with a first opening and another side, opposite to the first opening, is connected to the first tube body and the negative pressure source. The bone cement implantation system is a second needle tube, comprising a hollow second needle body and a second tube body. The second needle body has one side with a second opening, and another side, opposite to the second opening, is connected to the second tube body and the pushing pump.

In one embodiment of the present invention, the pushing system comprises a mixing device which is capable of adjusting the ratio of a plurality of the bone cement materials and then mixing the materials, and the mixing device electrically connected to the control system for accepting a control signal, generated from the control system by calculating a input signal of the sensor, to adjust the ratio of the bone cement materials for controlling the fluidity of the bone cement which is delivered through the bone cement implantation system.

In one embodiment of the present invention, the bone cement materials adjusted by the mixing device are selected from N, N-dimethyl-p-toluidine, hydroquinone, methyl methacrylate, calcium phosphate, calcium sulfate derivative, calcium oxide, calcium carbonate, calcium hydroxide, calcium magnesium phosphate, hydroxyapatite, calcium hydroxyapatite, calcium dihydrogen phosphate, calcium metaphosphate, phosphate derivative, dihydrate Calcium hydrogen phosphate, tricalcium phosphate, lactone polymer, amino acid polymer, anhydride polymer, orthoester polymer, acid anhydride imine copolymer, orthocarbonate polymer, polyhydroxyalkanoate, dioxane Hexone polymer, phosphate polymer, polylactic acid, mixed polylactic acid, polyglycolic acid, polylactic acid-glycolic acid, poly(L-lactic acid-lactic acid) copolymer, polylactic acid-polytrimethylene carbonate) Copolymer, polyhydroxybutyrate, polycaprolactone, polyvalerolactone, polybutyrolactone, polyacrylic acid, polycarboxylic acid, polyallylamine hydrochloride, polydiallyldimethyl chloride Ammonium, polyethyleneimine, polypropylene fumarate, polyvinyl alcohol, polyvinylpyrrolidone, polyethylene, polymethylester, carbon fiber, polyethylene glycol, polyethylene oxide, poly(2-ethyl-2-oxazole Porphyrin), polyethylene oxide polypropylene oxide block copolymer, polyethylene terephthalate polyamine, any one thereof or any combination thereof.

In one embodiment of the present invention, the bone cement injection system further comprises at least one set of trocars, comprising a first trocar, a second trocar and at least one connector, wherein the first trocar, comprising at least one first connecting portion, is sleeved on the first needle tube. When the first trocar is sleeved on the first needle tube, the extending direction of the at least one first connecting portion forms a first indication angle with the opening direction of the first opening; wherein the second trocar, comprising at least one second connecting portion, is sleeved on the second needle tube. When the second trocar is sleeved on the second needle tube, the extending direction of the at least one second connecting portion forms a second indication angle with the opening direction of the second opening; wherein the at least one connector is connected with the at least one first connecting portion and the at least one second connecting portion to restrict and fix the positions of the first needle tube and the second needle tube, and the first opening is adjusted to be disposed face to face with the second opening based on the first indication angle and the second indication angle.

In one embodiment of the present invention, the first opening and the second opening are an opening on one side or an opening on the bottom of a bent needle body.

In one embodiment of the present invention, when the at least one connecting portion is more than two, these connecting portions are disposed in the same extending direction.

In one embodiment of the present invention, the connector is integrally formed, sleeved on, screwed with the at least one first connecting portion and the at least one second connecting portion.

BRIEF DESCRIPTION OF THE DRAWINGS

The detailed structure, operating principle and effects of the present invention will now be described in more details herein after with reference to the accompanying drawings that show various embodiments of the present disclosure as follows.

FIG. 10 is a statistical diagram of the bone cement injection results of the present invention.

DETAILED DESCRIPTION OF THE INVENTION

Unless defined otherwise, all technical and scientific terms used herein have the same meaning as commonly understood by a person skilled in the art to which this invention belongs.

The traditional negative pressure bone cement injection device cannot accurately respond to the actual physiological conditions inside the spinal vertebral body, so there is a chance that the bone cement leads out during the bone cement injection process and causes complications. Therefore, the present invention provides a novel negative pressure guided bone cement injection system that can monitor the physiological conditions of the patient's spinal vertebral body and all the environmental parameters of the system, and then send the signals to the operator and the control system actively or passively for achieving the purpose of monitoring patients and controlling feedback.

Accordingly, the present invention provides a negative pressure guided bone cement injection system comprising the at least one sensing device disposed at a negative pressure system for sensing at least one environmental parameter and then sending the at least one environmental parameter to the control system. On the other hand, the system further comprises a mixing device for adjusting the ratio of a plurality of the bone cement materials and then mixing the materials to control the fluidity and the injection state of the bone cement. Furthermore, the system comprises a set of trocars for restricting and fixing the positions of the first needle tube and the second needle tube to adjust the first opening to be disposed face to face with the second opening, so that the efficiency of the system is increased.

Figure 1:
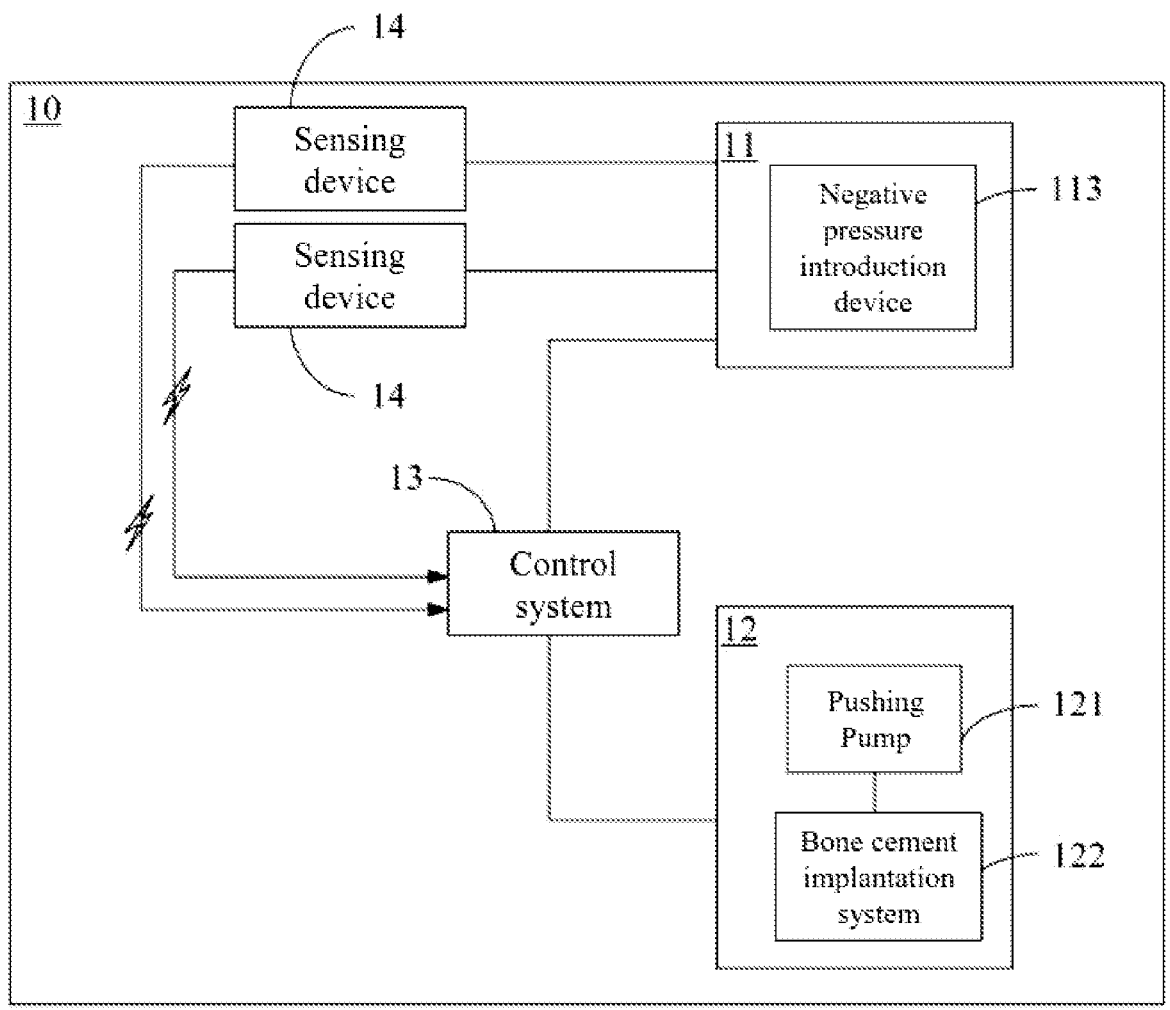
FIG. 1 is a system block diagram of a preferred embodiment of the negative pressure guided bone cement injection system provided by the present invention.

Refer to FIG. 1, a system diagram of a preferred embodiment of a negative pressure guided bone cement injection system provided by the present invention. The negative pressure guided bone cement injection system 10 comprises a negative pressure system 11, a pushing system 12, a control system 13, and at least one sensing device 14. The control system 13 is connected to and controls the negative pressure system 11 and the pushing system 12 respectively. If the control system 13 obtains at least one sensing parameter from the at least one sensing device 14, the control system 13 control the bone cement injection conditions of the negative pressure system 11 and the pushing system 12.

The negative pressure system 11 comprises a negative pressure introduction system 113 connected to a negative pressure source. The negative pressure introduction system 113 has a cavity (not shown) inside and an opening (not shown) located at the opposite side of the side connected to the negative pressure source. When the negative pressure introduction device 113 introduces a negative pressure from the negative pressure source, the negative pressure passes through the cavity (not shown) to the opening located at the opposite site to complete the negative pressure transmission. Therefore, the negative pressure system 11 provides the negative pressure as a power source for guiding the bone cement during the bone cement injection process, so that the bone cement is allowed to fill the target region uniformly without any leakage while the process of injecting the bone cement into the target region.

The pushing system 12 comprises a pushing pump 121 and a bone cement implantation system 122, wherein the pushing pump 121 is connected to the bone cement implantation system 122 for pushing a bone cement material in the bone cement implantation system 122 for delivery. Therefore, the pushing system 12 provides a positive pressure to push the bone cement into the target region directly for increasing the support of the target region, and the positive pressure of the pushing system 12 will determine the injection rate of injecting the bone cement into the target region.

The control system 13 is electrically connected to the at least one sensing device 14. If the at least one sensing device 14 disposed at any position of the negative pressure 11 system senses at least one environmental parameter, it will send the at least one environmental parameter to the control system 13. And the control system 13 will adjust and control the strength of the negative pressure of the negative pressure system 11 based on the at least one environmental parameter. On the other hand, the way that the control system 13 controls the strength of the negative pressure is the operator adjust the parameters provided by the control system 13 based on the operator's requirements, or a self-feedback mechanism, the control system 13 receives the at least one environmental parameter for making a calculation based on the information of the at least one environmental parameter to compare it with a preset ideal parameter, and the compared difference value is used as a reference to adjust the current strength of the negative pressure. The above strategies both are very convenient operation modes of the negative pressure guided bone cement injection system 10. Compared with the traditional way that operator has to adjust and control the strength of the negative pressure based on the operator's experience, the above strategies provide higher operational stability and have more precise and consistent operational response.

The at least one sensing device 14, disposed at any position of the negative pressure system 11 of the said system 10, allows the operator or the system itself (such as the control system 13) to understand the operation situation, the environmental situation and the instant change in the strength of the negative pressure of the negative pressure system 11, and even obtain the bone cement delivery situation of the pushing system 12 indirectly from the above information for adjusting the strength of the negative pressure correspondingly. Compared with other types of bone cement injectors, including a bone cement injection system with negative pressure guide but without sensing device, in this industry, the negative pressure guided bone cement injection system 10 provided by the present invention can accurately control and adjust the negative pressure's effect on injecting the bone cement into target region to make the whole injection process smoother and avoid any leakage caused by improper negative pressure. While adjusting other large adjustment value, some quite small values, like adjusting and sensing the strength of the negative pressure, that indirectly affect the injection of the bone cement are still obtained. On the other hand, when the sensing position is far away from the actual bone cement injection end, the changes in surrounding environmental parameters are simpler, so the obtained measurement values are more accurate as well. Hence, the strength of the negative pressure can be adjusted much precisely to evaluate the operational convenience of the injection system.

Specifically, the bone injection system provided by the present invention can combine the initial pressure value of the injection target region with the information of the radiography to determine whether the patient is suitable for receiving the negative pressure guidance or traditional forming surgery, or through the mechanism of measurement and feedback control, the increase of internal pressure in the injection target region can be accurately determined and the feedback of the amount of the bone cement in the injection target region can also be well evaluated to decide the time to stop injection during the repeated process of continuous injection and solidification of bone cement. All the above can effectively avoid the high risk of leakage. On the other hand, because the bone cement may coagulate in the vertebral body or between the pipelines during the suction process, it is difficult to confirm the pressure difference between the two ends of the vertebral body and the increase of the pressure is whether because of the filling completion or the pipelines are blocked. Therefore, the at least one sensing device 14 is disposed at the negative pressure system 11 for providing sensing data different from the prior art and give higher detection accuracy. The at least one environmental parameter sensed by the at least one sensing device 14 includes a viscosity of the bone cement material, a flow rate of the bone cement, a density of the bone cement material, a bone density, a negative pressure in the negative pressure introduction device, a negative pressure in the negative pressure system or a negative pressure in a target region.

Figure 2:
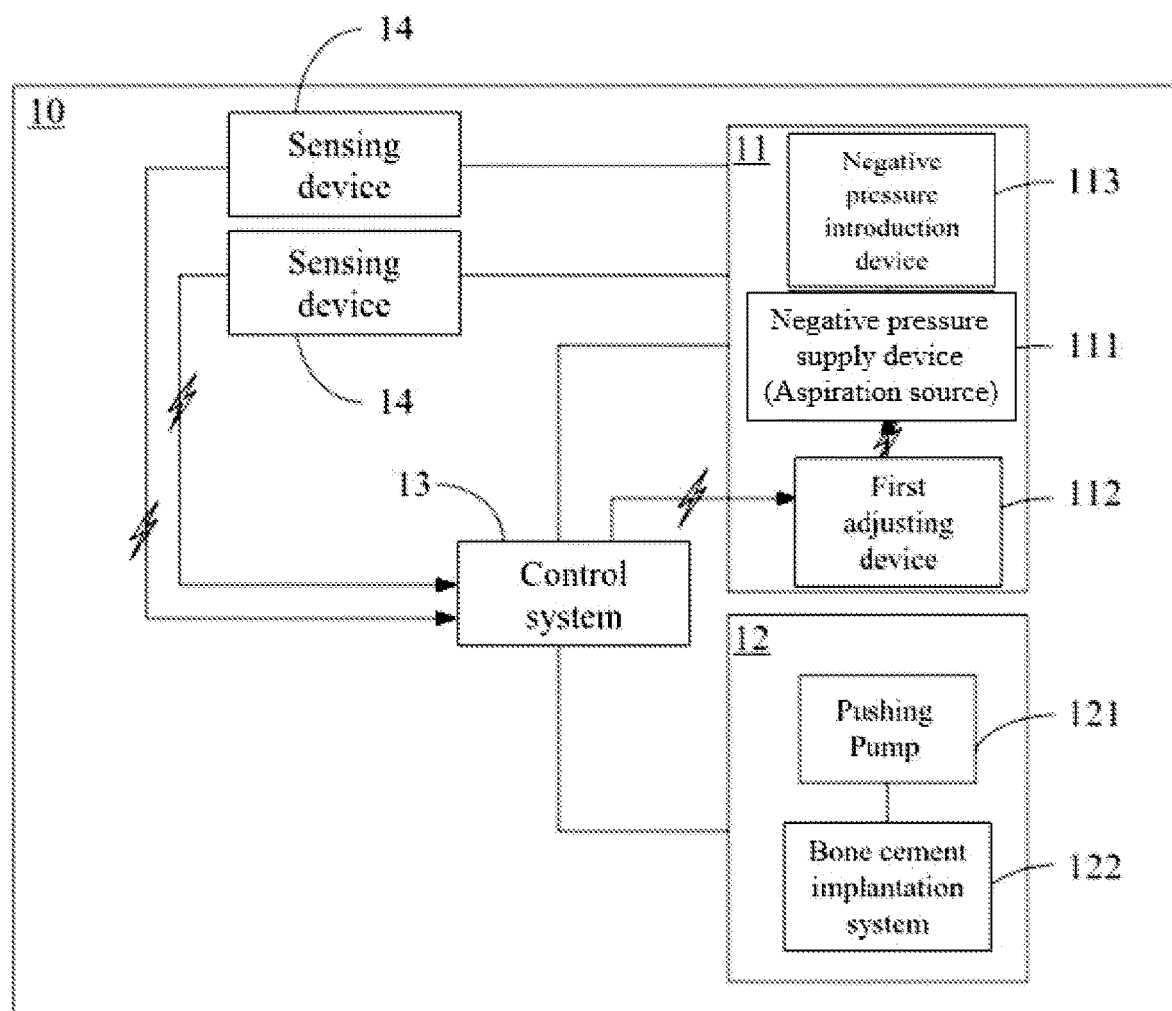
FIG. 2 is a system block diagram of a preferred embodiment of the negative pressure guided bone cement injection system provided by the present invention.

Refer to FIG. 2, a system block diagram of a preferred embodiment of the negative pressure guided bone cement injection system provided by the present invention. As shown in the figure, the negative pressure system 11 in the said system comprises a negative pressure supply device 111, a first adjusting device 112. The negative pressure supply device 111, connected to the first adjusting device 112, is configured to provide a negative pressure and receives the regulation of the first adjusting device 112 to adjust the output negative pressure of the negative pressure supply device 111. On the other hand, the negative pressure supply device 111 is connected to a negative introduction device 113. When the negative pressure introduction device 113 introduces the negative pressure provide by the negative pressure supply device 111, the negative pressure passes through the cavity (not shown) to the opening (not shown) located at the opposite site to complete the negative pressure transmission. The first adjusting device 112 is electrically connected to the control system 13. When the at least one sensing device 14, disposed at any position of the negative pressure system 11, senses at least one environmental parameter, it sends the at least one environmental parameter to the control system 13. Then, the control system 13 provides an indication signal to the first adjusting device 112 based on the information of the at least one environmental parameter to control the strength of the negative pressure provided by the negative pressure system 11. Therefore, the control system 13 is configured to control the strength of the negative pressure provided by the negative pressure system 11 by adjusting the first adjusting device 112 electrically connected to the negative pressure supply device 111. Based on these principles, the negative pressure supply device is a negative pressure pump or a medical negative pressure socket. Through the configurations of the negative pressure supply device 111 and the first adjusting device 112, the negative pressure guided bone cement injection system 10 provided by the present invention can accelerate the injection of the bone cement into the target region and keep the bone cement flowing without stagnating for reducing the possibility of bone cement solidification.

Figure 3:
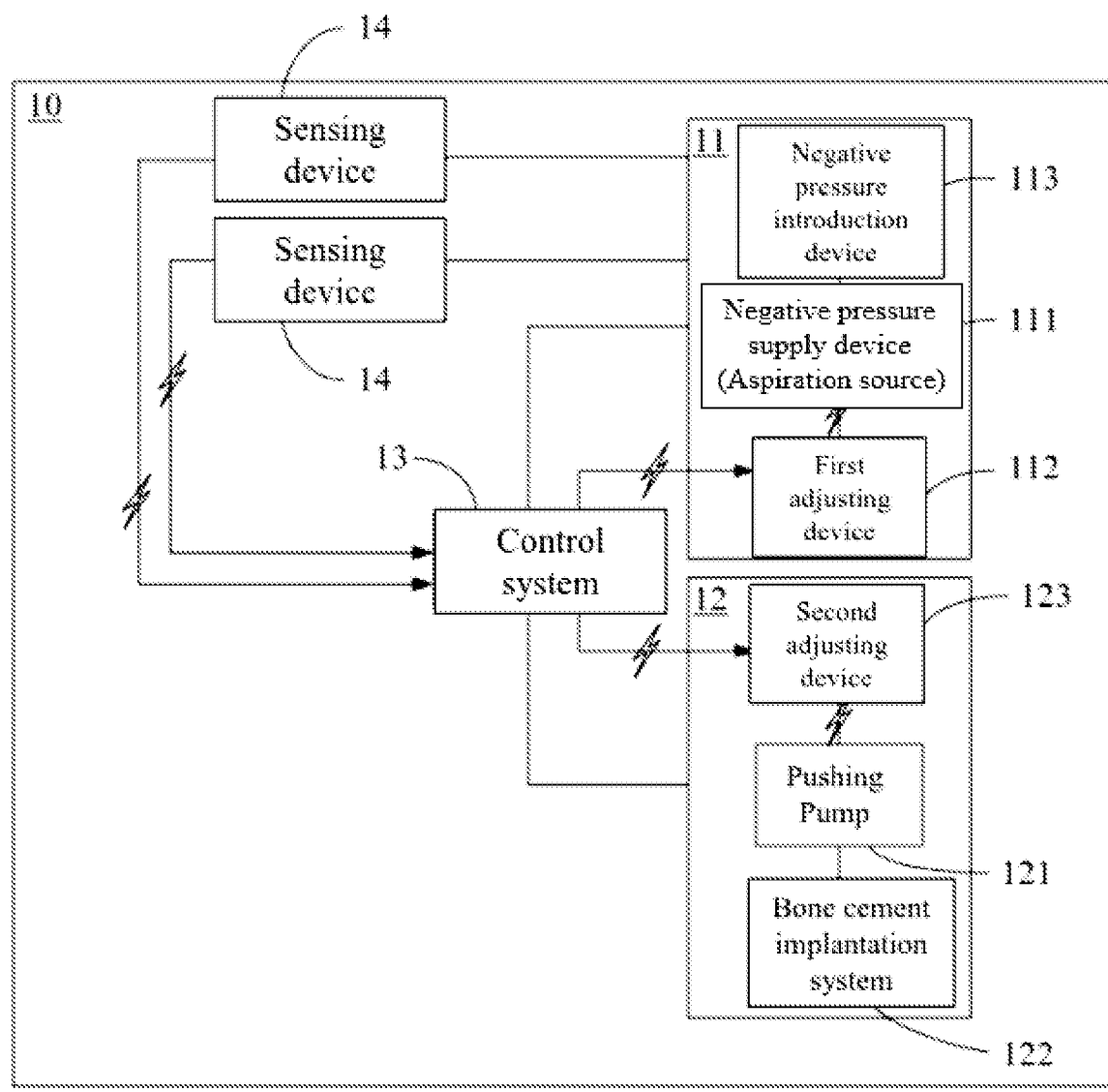
FIG. 3 is a system block diagram of a preferred embodiment of the negative pressure guided bone cement injection system provided by the present invention.

Please refer to FIG. 3, a system block diagram of a preferred embodiment of the negative pressure guided bone cement injection system provided by the present invention. As shown in the figure, the pushing system 12 further comprises a second adjusting device 123 electrically connected to the pushing pump 121 and the control system 13 for being controlled by the control system 13 and adjusting the pushing strength of the pushing pump 121 on the bone cement material.

The first adjusting device 112 and the second adjusting device 123 are configured to adjust the output of the negative pressure supply device 111 and the pushing pump 121 respectively. The adjusting devices adjust the parameters of pumps like altering the vacuum degree inside of the pumps or the current flow or the voltage of the pumps by controlling the flow rate, pressure, temperature or liquid level of the pumps for adjusting the supply of the negative pressure or the bone cement material provided by the negative pressure supply device 111 and the pushing pump 121 effectively. In a preferred embodiment of the present invention, the first adjusting device and the second adjusting device are a flow regulating valve, a current regulator or a voltage regulator.

Figure 4:
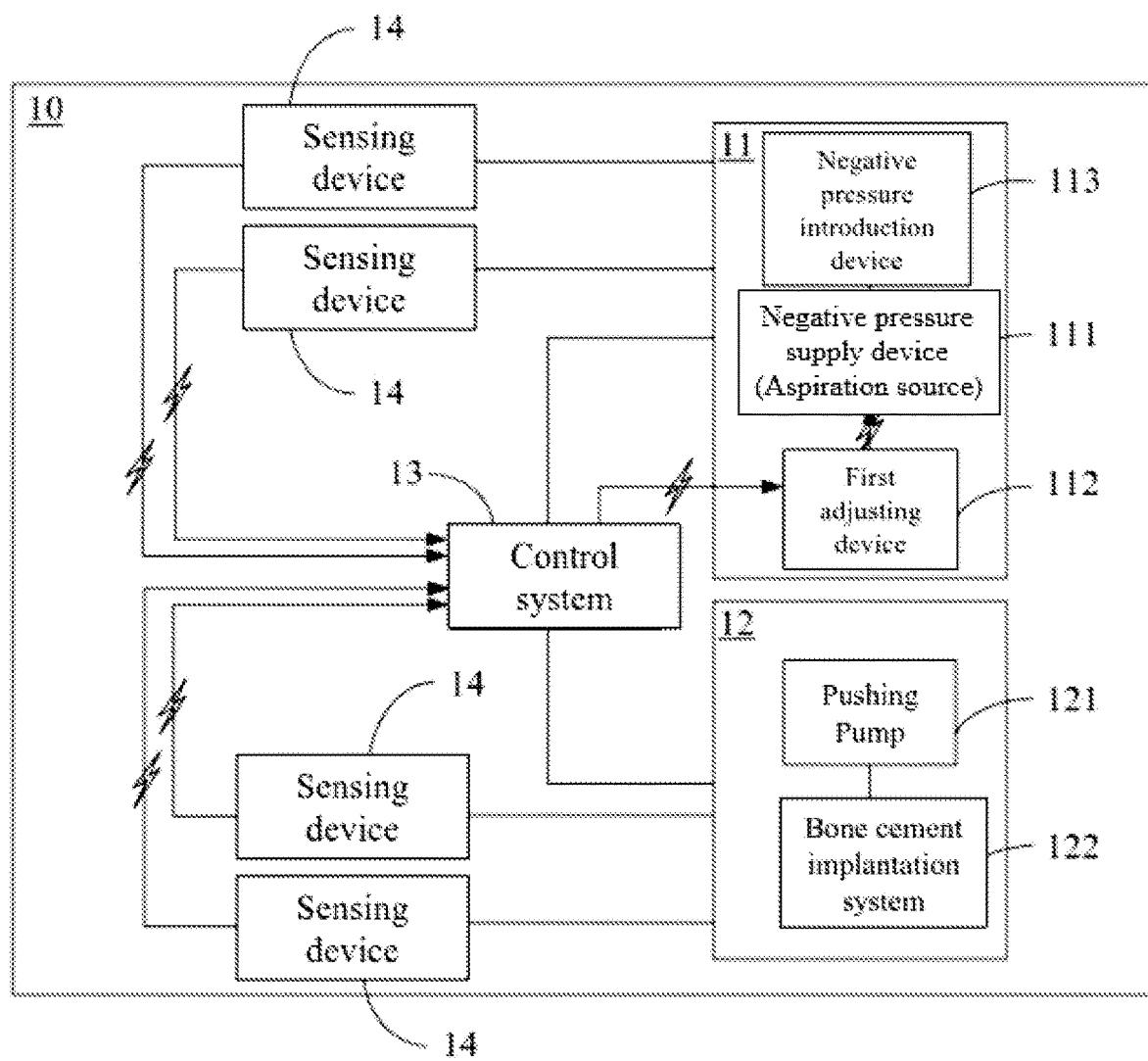
FIG. 4 is a system block diagram of a preferred embodiment of the negative pressure guided bone cement injection system provided by the present invention.

As shown in the FIG. 4, a system block diagram of a preferred embodiment of the negative pressure guided bone cement injection system provided by the present invention. The at least one sensing device 14 is disposed at the negative pressure system 11 and the pushing system 12 for sensing the at least one environmental parameter of the negative pressure 11 system and the pushing system 12 and sending the at least parameter to the control system 13 to adjust and control the negative pressure guided bone cement injection system 10. For example, a flow rate sensing device, a viscosity sensor or a pressure sensor can be disposed, wherein the pressure sensor is disposed between the pushing pump 121 and the bone cement implantation system 122 instead of the inside of the bone cement injection devices, because the bone cement material will gradually solidify during the injection process. Therefore, to estimate the bone cement injection pressure, if the pressure in the bone cement implantation system 122 rises, the resistance for pumping system 121 will increase and the pumping force will also increase, so that the pressure on the pressure sensor located at the between will increase as well.

During the bone cement injection process, the bone cement will gradually solidify and increase the resistance to the pump, so the distance that can be pushed will reduce and the injection rate will drop as well. Therefore, the at least one sensing device 14 can be disposed at the pushing pump 121 for sensing the condition of the pushing pump 121 and sending it to control system 13 for adjusting the pumping strength to keep the injection rate staying at the same level instead of decreasing caused by the bone cement solidification, and the at least one sensing device 14 is a motor state sensing device.

Disposing the at least one sensing device 14 on the negative pressure system 11 and the pushing system 12 allows the negative pressure guided bone cement injection system 10 to not only evaluate the bone cement injection situation based on the related environmental parameters from the negative pressure system 11, but also determine the bone cement injection situation much accurately referring to the relevant environmental parameters from the pushing system 12 at the same time. And the relevant environmental parameters from the pushing system 12 are the reference values closer to the bone cement infection end, which can complement the insufficiency caused by only evaluating the related environmental parameters from the pushing system 12.

Moreover, disposing the at least one sensing device 14 on the negative pressure system 11 and the pushing system 12 allows the negative pressure guided bone cement injection system 10 cross compares the environmental parameters obtained from two ends by the control system 13 to obtain the interactional relationship between the negative pressure system 11 and the pushing system 12. For example, when the operator adjusts the strength of the negative pressure of the negative pressure system 11, the control system 13 can monitor the change in the bone cement flow rate in the pushing system 12 in time to see the effect of the change in the strength of the negative pressure on the rate of the bone cement injection overall. The other example, when a blockage is formed at the target region, the control system 13 can analyze the effects of the blockage condition on the negative pressure and the bone cement supply and delivery by the environmental sent from the at least one sensing device 14, disposed on the negative pressure system 11 and the pushing system 12, to determine how to adjust the strength of the negative pressure of the negative pressure system 11 and the pumping strength of the pumping system 12 for improving the efficiency of bone cement injection. Another example, when the at least one sensing device 14 disposed at the end of the negative pressure system and the bone cement injection end is a pressure sensor, the pressure difference between the two sides of the target region can be sensed, which can be used as a reference to evaluate how much of the pressure value does the bone cement material receive for ensuring the fluid in the cavity is guided by a stable pressure, and a standard for determining if the procedure should be continued or not. When the pressure rises during the injection process because the cavity is filled up and reaches the measurement threshold of the injection system, it indicates that the filling of the bone cement at the target region is completed, or when the environment of the target region is blocked, it will cause the pressure value of the negative system increase and be determined that is inoperable. Therefore, by the present invention, the system has a feedback mechanism that works quickly and provides indications for the system itself to determine when to start operation and complete operation.

Therefore, the at least one environmental parameter described in the present invention comprises a viscosity of the bone cement material, a flow rate of the bone cement, a density of the bone cement material, a bone density, a negative pressure in the negative pressure introduction device, a negative pressure in the negative pressure system or a negative pressure in a target region.

In the preferred embodiment of the present invention, the at least one sensing device 14 senses at least one environmental parameter and send it to the control system 13 for calculating and generating an operation result that is considered for adjusting the strength of the negative pressure of the negative pressure system 11 and/or the pumping strength of the pumping system 12. For example, when the at least one sensing device 14 of the negative pressure system 11 obtains a value of the negative pressure is as same as the preset ideal value of the negative pressure, the pushing pump 12 will start push the bone cement for injection. At the same time, the at least one sensing device 14 keep sensing the change in the value of the negative pressure during the injection process, if the value of the negative pressure keep dropping, it will send this result to the control system 13 and the control system 13 will regulate the first adjusting device 112 to increase the value of the negative pressure or regulate the second adjusting device 123 to decrease the pumping strength as an active regulation to adjust the whole bone cement injection process.

Figure 5:
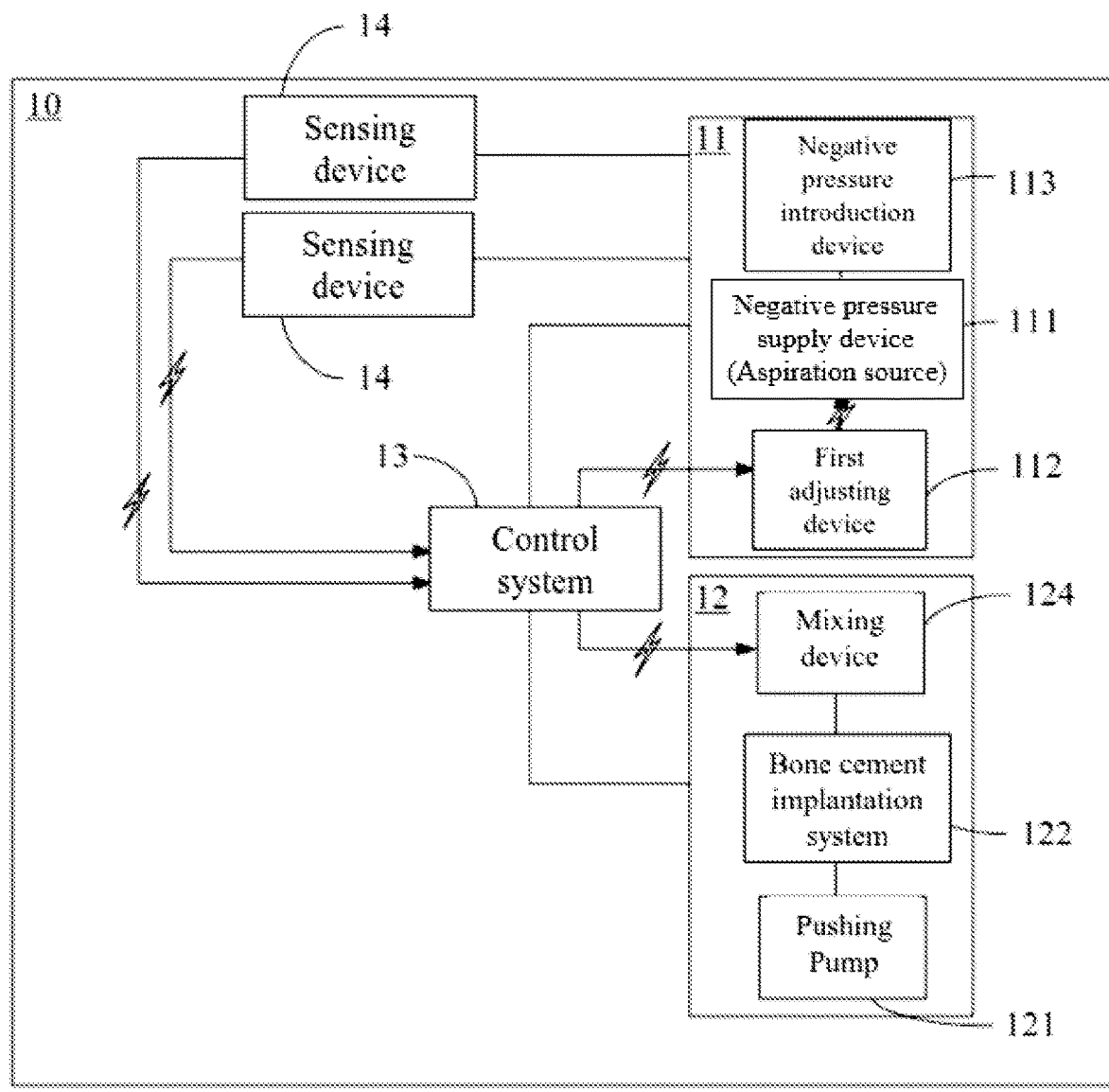
FIG. 5 is a system block diagram of a preferred embodiment of the negative pressure guided bone cement injection system provided by the present invention.

Refer to FIG. 5, a system block diagram of a preferred embodiment of the present invention. In order to provide a more versatile adjustment mode for adjusting the injection rate of bone cement to avoid blocking, the pushing system 12 of the said system 10 further comprises a mixing device 124, comprising a container that can contain a plurality of bone cement materials, a mixing tank and a stirring element, for adjusting the ratio of a plurality of the bone cement materials and then mixing the materials to provide a bone cement material with variable viscosity and fluidity. On the other hand, the mixing device 124 is electrically connected to the control system 13 which adjusts the ratio of the bone cement materials to control the fluidity of the bone cement which is delivered through the bone cement implantation system 122. Therefore, the control system can provide an instruction to the mixing device 124 to adjust the ratio of the bone cement materials to change the fluidity property after receiving the at least one environmental parameter obtained from the at least one sensing device 14, so that the said system 10 can improve the flow rate of the bone cement without changing the strength of the negative pressure or pumping strength of the pumping system to provide a suitable delivery rate of bone cement.

For example, the mixing device 124 can comprise a plurality of accommodation tank for placing a plurality of bone cement materials, and each of the accommodation tank has an outlet that can be controlled to open and close. And a mixing tank, combined with a weighing tool, receives and weighs the bone cement materials falling from the outlet for ensuring the ratio and the weights of the bone cement materials. Finally, the bone cement materials in the mixing tank are mixed by a stirring element and then delivered to the bone cement implantation system 112. The mixed bone cement material will be injected to the target region through the bone cement implantation system 112 by pushing by the pushing pump 121.

And in a preferred embodiment of the present invention, the bone cement materials that adjusted by the mixing device 124 are selected from N, N-dimethyl-p-toluidine, hydroquinone, methyl methacrylate, calcium phosphate, calcium sulfate derivative, calcium oxide, calcium carbonate, calcium hydroxide, calcium magnesium phosphate, hydroxyapatite, calcium hydroxyapatite, calcium dihydrogen phosphate, calcium metaphosphate, phosphate derivative, dihydrate Calcium hydrogen phosphate, tricalcium phosphate, lactone polymer, amino acid polymer, anhydride polymer, orthoester polymer, acid anhydride imine copolymer, orthocarbonate polymer, polyhydroxyalkanoate, dioxane Hexone polymer, phosphate polymer, polylactic acid, mixed polylactic acid, polyglycolic acid, polylactic acid-glycolic acid, poly(L-lactic acid-lactic acid) copolymer, polylactic acid-polytrimethylene carbonate) Copolymer, polyhydroxybutyrate, polycaprolactone, polyvalerolactone, polybutyrolactone, polyacrylic acid, polycarboxylic acid, polyallylamine hydrochloride, polydiallyldimethyl chloride Ammonium, polyethyleneimine, polypropylene fumarate, polyvinyl alcohol, polyvinylpyrrolidone, polyethylene, polymethylester, carbon fiber, polyethylene glycol, polyethylene oxide, poly(2-ethyl-2-oxazole Porphyrin), polyethylene oxide polypropylene oxide block copolymer, polyethylene terephthalate polyamine, any one thereof or any combination thereof.

Figure 6:
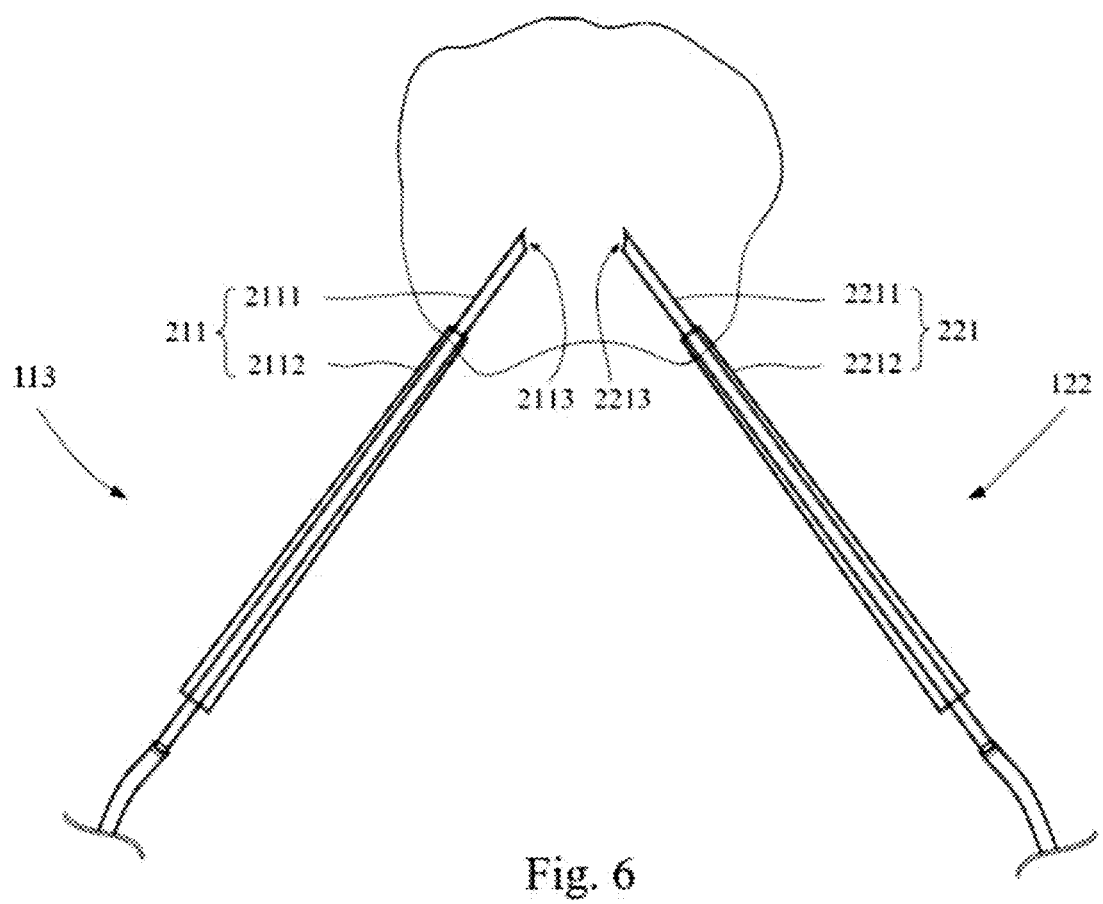
FIG. 6 is a schematic view showing a preferred embodiment of the negative pressure guided bone cement injection system provided by the present invention.

Refer to FIG. 6, a schematic view showing a preferred embodiment of the present invention. In order to make the said system 10 more convenient to hold and operate. As shown in the preferred embodiment of the present invention, the negative pressure introduction device 113 is a first needle tube 211 comprising a hollow first needle body 2111 and a first tube body 2112 and both are connected. The first needle body 2111 has a first opening 2113 located at the opposite side of which is connected to the first tube body 2212. And the bone cement implantation system 122 is a second needle tube 221, comprising a hollow second needle body 2211 and a second tube body 2212 and both are connected. The second needle body 2211 has a second opening 2213 located at the opposite side of which is connected to the second tube body 2212, and the second tube body 2212 has a side, the opposite side of the side connected to the second needle body 2211, connected to the pushing pump 121. Therefore, the said system 10 can utilize a thinner and penetrating needle to operate at the target region and reduce the damage to healthy region. In the meanwhile, the soft tube body can adapt to different operating environments and is a good option for introducing negative pressure or bone cement materials.

Figure 7A:
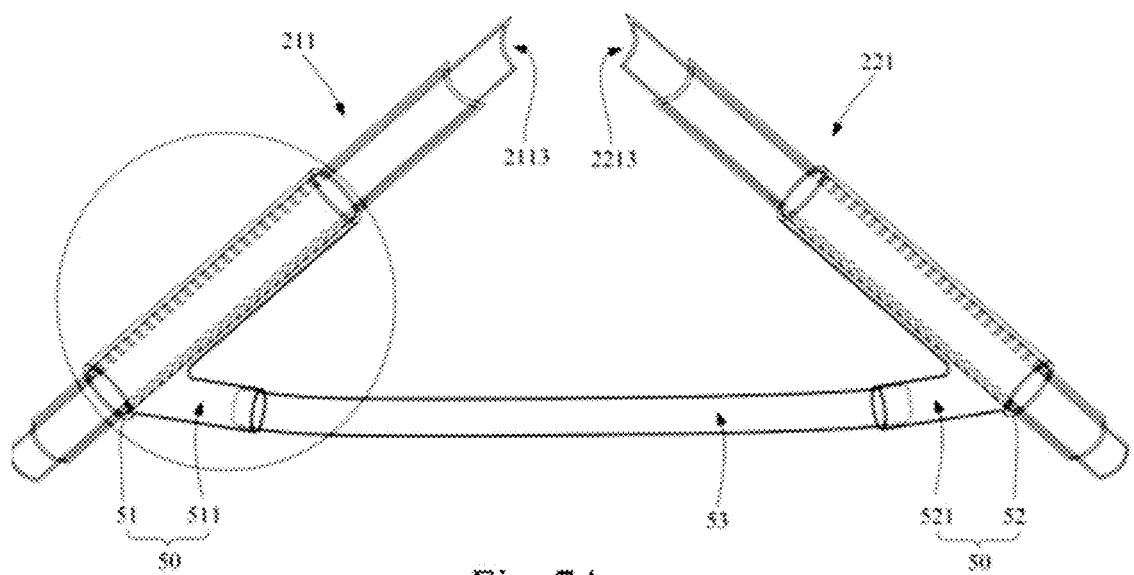
FIG. 7A is a cross-sectional view showing a preferred embodiment of the negative pressure guided bone cement injection system provided by the present invention.
Figure 7B:
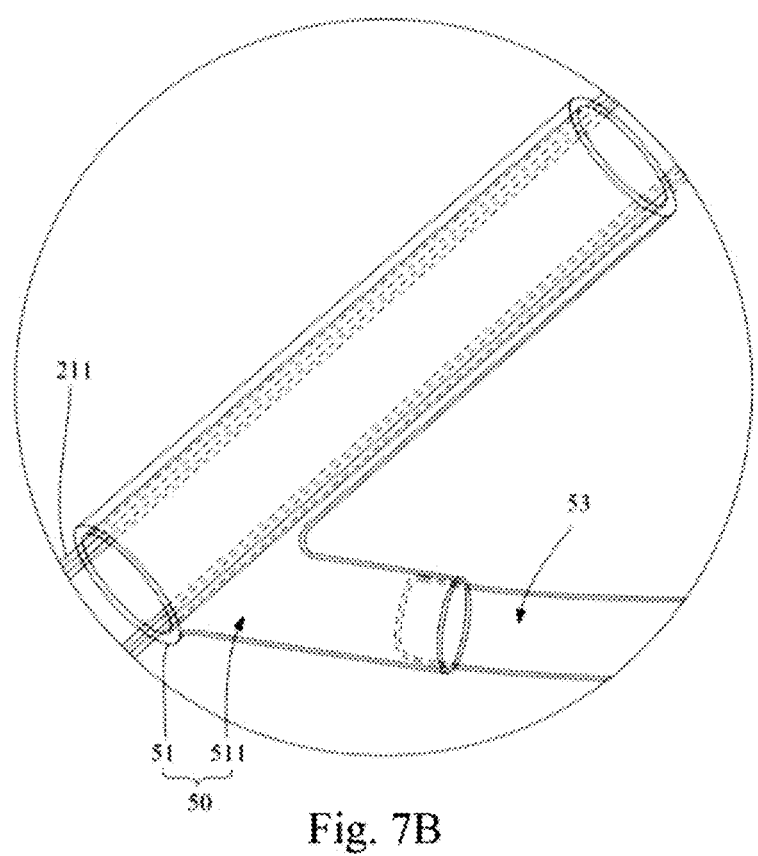
FIG. 7B is a partial enlarged view of FIG. 7A.

In order to optimize the negative pressure guiding efficiency of the said system 10, an auxiliary component is provided to provide a reference angle for the operator to ensure these openings are disposed face to face and provide a firm force to hold the arrangement of the negative pressure introduction device 113 and the bone cement implantation device 122 in a preferred embodiment of the present invention. Therefore, referring to FIG. 7A-7B, a cross-sectional view and a partial enlarged view showing a preferred embodiment of the present invention, the embodiment with the needle tube set further comprises a set of trocars 50 for being sleeved on the first needle tube 211 and the second needle tube 221. The set of trocars 50 comprises a first trocar 51, with at least one first connecting portion 511, is sleeved on the first needle tube 211. When the first trocar 51 is sleeved on the first needle tube 211, the extending direction of the at least one first connecting portion 511 forms a first indication angle with the opening direction of the first opening 2113. In addition, the set of trocars 50 further comprises a second trocar 52, with at least one second connecting portion 521, is sleeved on the second needle tube 221. When the second trocar 52 is sleeved on the second needle tube 221, the extending direction of the at least one second connecting portion 521 forms a second indication angle with the opening direction of the second opening 2213. Furthermore, the set of trocars 50 comprises at least one connector 53 connected to the at least one first connecting portion 511 and the at least one second connecting portion 521 to restrict and fix the positions of the first needle tube 211 and the second needle tube 221, so the first indication angle and the second indication angle is fixed as well, and the first opening is adjusted to be disposed face to face with the second opening based on the first indication angle and the second indication angle.

Figure 7C:
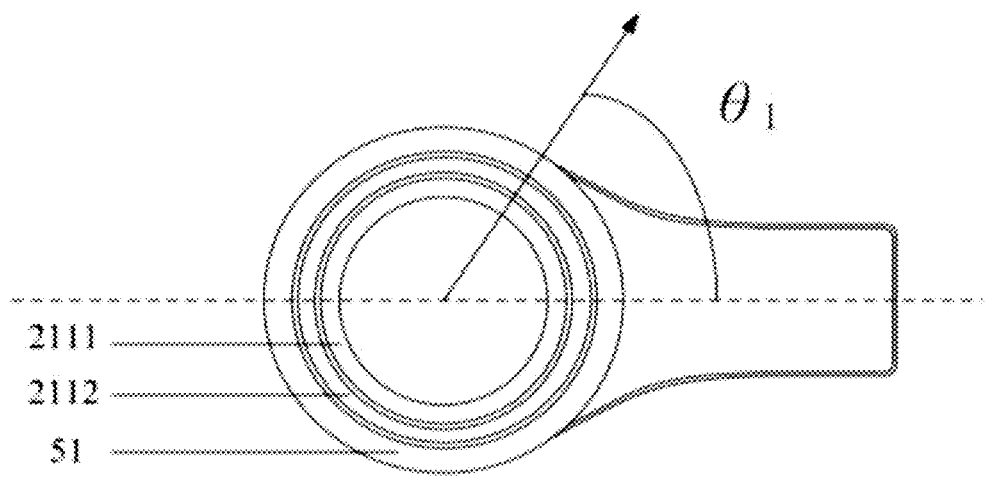
FIG. 7C-7E is an angle schematic view showing a preferred embodiment of the negative pressure guided bone cement injection system provided by the present invention.
Figure 7D:
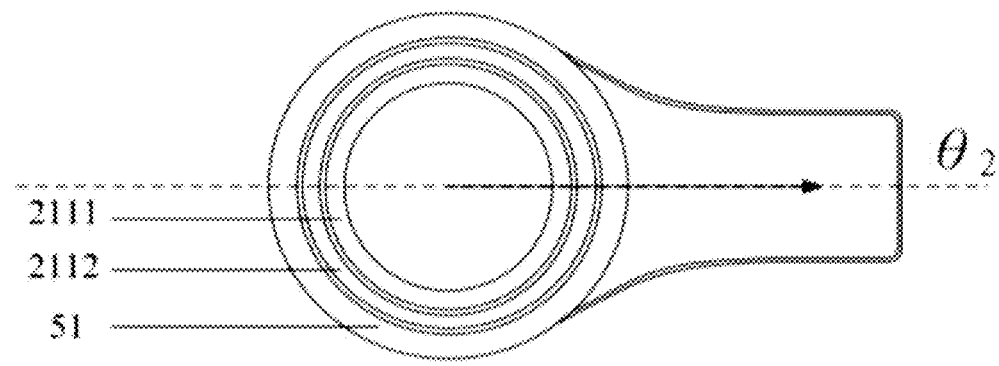
Figure 7E:
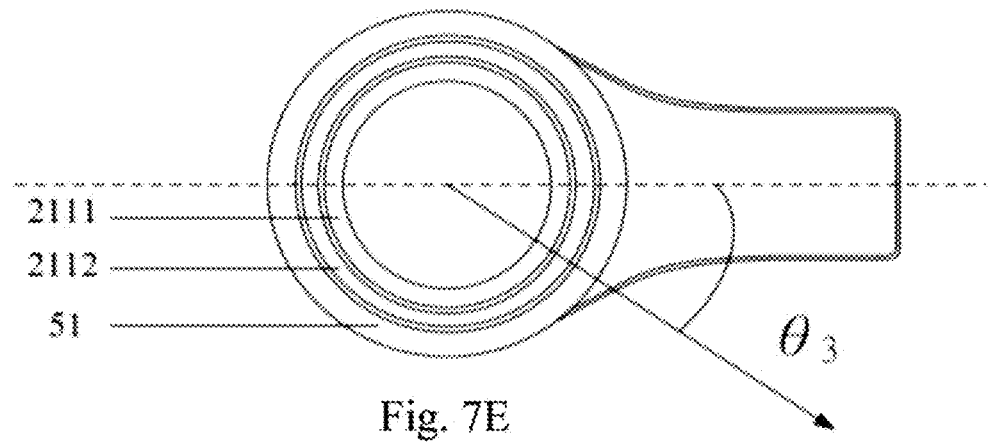

By the first indication angle and the second indication angle, the operator can be sure of the opening directions of the first opening 2113 and the second opening 2213 without seeing both. For example, referring to FIG. 7C-7E, when the first trocar 51 is sleeved on the first needle tube 211, if the extending direction of the first connecting portion 511 is as same as the opening direction of the first opening 2113, the first indicating angle will be 0 degrees (FIG. 7D 02). However, if the extending direction of the first connecting portion 511 is different from the opening direction of the first opening 2113, the angles θ1 and θ3 will be formed as shown in FIGS. 7C and 7E. The same rules can be applied on the second trocar 52 and the second needle tube 221. When the second trocar 52 is sleeved on the second needle tube 221, if the extending direction of the second connecting portion 521 is as same as the opening direction of the second opening 2213, the second indicating angle will be 0 degrees. Therefore, when the first needle body 2111 and the second needle body 2211 are in the target region and the opening direction cannot be ensured, the operator can confirm the extending direction of the first connecting portion 511 and the second connecting portion 521 to be sure of the opening directions of the first opening 2113 and the second opening 2213. And in the meanwhile, the connector 53 can restrict and fix the positions of the first needle tube 211 and the second needle tube 221, so the opening directions of the first opening 2113 and the second opening 2213 are fixed as well and these openings are ensured that they are disposed face to face.

Therefore, in the present invention, the first opening 2113 and the second opening 2213 need to be disposed face to face in the operation of the said system 10. In order to enable the said system to have a smaller operating angle, the first opening and the second opening are an opening on one side or an opening on the bottom of a bent needle body in a preferred embodiment of the present invention. In this way, when these openings are at the bottom of the needles and disposed face to face, the angle between the first needle tube 211 and the second tube 221 would be 180 degree and it would increase the operational difficulty.

In a preferred embodiment of the present invention, to make sure the extending directions of these connecting portions can indicate the relative positional relationships between the first opening 2113 and the second opening 2213 while the trocar set 50 is sleeved on the first needle tube 211 and the second needle tube 221, the trocar set can further comprise two or more connecting portions disposed in the same extending directions, so that the at least one connector 53 can connect all these connecting portions in the same way without deviation. Therefore, even if the operator cannot see the first opening 2113 and the second opening 2213, the operator still can understand the angle correspondence between these connecting portions and these openings. And the structural connection between the at least one first connecting portion 511 and the at least one second connecting portion 521 will be reinforce without change in the indication angle due to rotation or sliding.

In addition, in order to make the trocar set 50 more convenient to match the first needle tube 211 and the second needle tube 221, the trocar set 50 can be set at a fixed angle and then sleeved on the first needle tube 211 and the second needle tube 221, or the first trocar 51 and the second trocar 52 are sleeved on the first needle tube 211 and the second needle tube 221 and then the at least one connector 53 set between the first trocar 51 and the second trocar 52 and the at least one first connecting portion 511 and the at least one second connecting portion 521. Based on these principles, in the said system 10 provided by this invention, the connector 53 is connected to the least one first connecting portion 511 and the at least one second connecting portion 521, and the connection way is integrally formed with the trocar set in the indication angle, or sleeved on, screwed with the trocar set in an active way to set the relationship of the indication angles of these connecting portions and these openings.

In summary, the present invention provides a negative pressure guided bone cement injection system that can instantly obtain environmental parameters in the operating system during bone cement injection and send it to the control system as a reference, and the injection conditions can be changed for different operation condition as a precision medicine. On the other hand, the said system can increase it's efficiency by different additional devices, including providing a mixing system to adjust the ratio of the bone cement material for controlling the fluidity properties as an adjustment of the injection condition, and providing a set of trocars to restrict and fix the positions of the first needle tube and the second needle tube, and adjust the first opening to be disposed face to face with the second opening. The present invention increases the guiding efficiency of the bone cement and overcomes the clogging and leaking problem of the traditional injection system.

The present invention is further illustrated by the following examples, which are provided for the purpose of demonstration rather than limitation.

Embodiment 1. Establishment of a Negative Pressure Guided Bone Cement Injection System The negative pressure guided bone cement injection system of the present invention provides a negative pressure pump with a gas flow regulating valve as a negative pressure source for guiding, and the negative pressure pump is connected to a needle tube with an introduction opening on the other end for introducing the negative pressure to the target region. On the other hand, the bone cement injection pump is with a current regulating valve for controlling the positive pressure of the bone cement injection pump, and the bone cement injection pump is also connected to a needle tube with an introduction opening on the other end for injecting bone cement to the target region.

This embodiment also provides a set of trocars comprising a pair of trocars which can be respectively sleeved on the needle tube of the negative pressure system and the bone cement injection system. The sleeve way is moving from the thinner part of the needle body upwardly to the thicker part of the needle body and carded. And then the extending connecting portion forms an indication angle with the opening of the needle tube; therefore, when operator cannot see the opening of the needle tube because the needle tube is inside of the target region, operator can determine the opening of the needle tube by the externally part of the trocar to make sure the opening for introducing negative pressure is disposed face to face with the opening for injecting bone cement.

For the sensing device, a pressure sensing device is disposed at the front end of the needle tube of the negative pressure pump to sense the value of the negative pressure in the target region; and a micro ultrasonic probe is used to observe the bone density of the target region for evaluating the resistance state of the target region in order to adjust the strength of the negative pressure or the injection rate of the bone cement. On the other hand, a bone cement pressure sensor, a flow rate sensor and a viscosity sensor are disposed at the needle tube of the bone cement injection end to observe the injection state of bone cement as a basis for adjustment. And a plurality of pressure sensors is also disposed on the pressure sensing needle tube to observe the difference of negative pressure value in each section of the negative pressure system for determining whether the negative pressure needs to be increased or decreased.

In addition, the negative pressure guided bone cement injection system of the embodiment is also connected with a micro processing system, which can recode and analyze the signals of the target region, the negative pressure system and the bone cement injection system, and integrate relevant data to evaluate the current efficiency of bone cement injection and send adjust instructions or notification for adjusting the strength of the negative pressure, injection rate of bone cement or viscosity of bone cement materials.

Embodiment 2. Establishment of Control System in the Negative Pressure Guided Bone Cement Injection System When the negative pressure guided bone cement injection system provided in Embodiment 1 is turned on, the negative pressure pump in the negative pressure system start to operate, and the pressure sensor at the front end of the needle tube can measure an initial negative pressure value and send it to the micro processing system and compared with the negative pressure threshold (570 mmHg) preset by the micro processing system. If the negative pressure value obtained by the senor exceeds the preset threshold, the negative pressure motor and the bone cement pushing motor will stop operating. Conversely, if the measured negative pressure value is lower than the preset threshold, the micro processing system starts to drive the bone cement pushing motor for bone cement injection. And the micro processing system will keep observing the negative pressure value of the negative pressure needle tube and the pushing pressure value (positive pressure) of the bone cement injection needle tube. The operator can observe the condition of bone cement injection by reading the negative pressure value. If the negative pressure value is 0, it indicates that the pipeline may have abnormal connection such as falling off; and when the negative pressure value exceeds a target value (preset as 475 mmHg), it means the bone cement injection is completed.

On the other hand, when the negative pressure value does not reach the target value (preset as 475 mmHg), the relationship between the negative pressure value of the negative pressure needle tube and the pushing pressure value (positive pressure) of the bone cement injection needle tube will be further evaluated. These values and the values obtained by the flow rate sensor and the viscosity sensor will be sent to the micro processing system as an auxiliary judgment basis for the micro processing system to decide how to adjust the negative pressure value of the negative pressure motor. In this embodiment, when the positive pressure value of the bone cement injection needle tube does not exceed the negative pressure value of the end the negative pressure needle tube, the operating speed of the negative pressure motor will be increased to elevate the provided negative pressure; however, when the positive pressure value of the bone cement injection needle tube exceeds the negative pressure value of the end the negative pressure needle tube, the operating speed of the negative pressure motor will be decreased to reduce the provided negative pressure. And when the flow rate obtained by the flow rate sensor disposed at the needle tube of the bone cement injection end and the viscosity observed by the viscosity sensor are too high, the negative pressure motor will provide a larger negative pressure for guiding.

Embodiment 3. Evaluation of Bone Cement Injection Efficiency of the Negative Pressure Guided Bone Cement Injection System A total of 256 surgery cases from 159 patients with thoracic lumbar osteoporotic compression fractures including vertebrolasty (69 patients, 101 surgeries) or vesselplasty (90 patients, 155 surgeries) were enrolled. Each of the two surgeries type were divided into three types of operation, including one-way bone cement injection group, two-way bone cement injection group and two-way bone cement injection with negative pressure guidance group. The respective cases number of the six groups are listed, including a total of 26 cases of the vertebrolasty with one-way bone cement injection group (Condition 1), a total of 36 cases of the vesselplasty with one-way bone cement injection group (Condition 2), a total of 25 cases of the vertebrolasty with two-way bone cement injection group (Condition 3), a total of 41 cases of the vesselplasty with two-way bone cement injection group (Condition 4), a total of 50 cases of the vertebrolasty with two-way bone cement injection with negative pressure guidance group (Condition 5) and a total of 78 cases of the vesselplasty with two-way bone cement injection with negative pressure guidance group (Condition 6). After the surgery, the injection of bone cement was observed by X-ray film, and the distribution of the bone cement were ranked into excellent, good, poor and failed four levels determined by whether the bone cement crosses the vertebral midline. All relevant results were statistically tabulated, and the effects of different bone cement injection methods on the surgical results were observed and evaluated.

Figure 8:
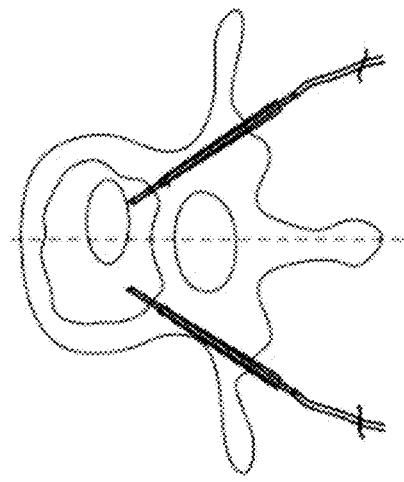
FIG. 8 is a schematic view showing the bone cement injection condition of the present invention.
Figure 8:
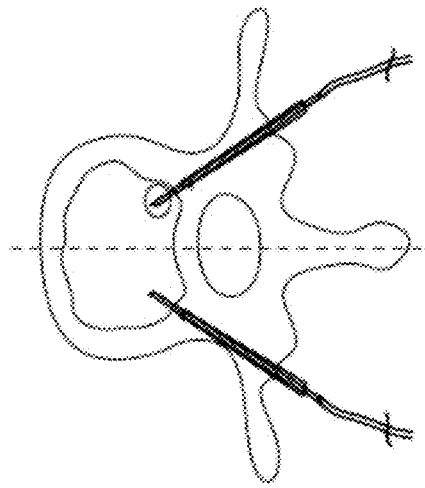
Figure 8:
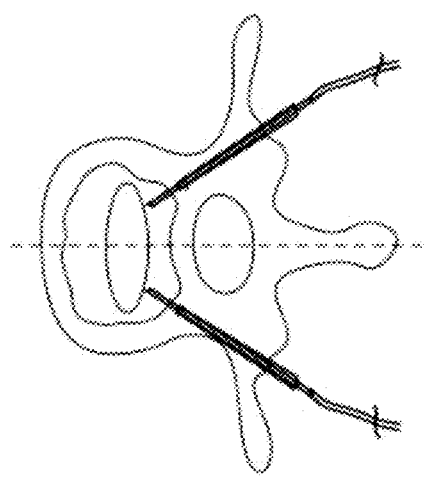
Figure 8:
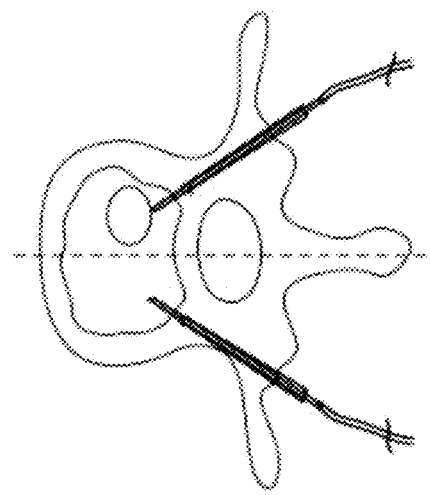
Figure 9C:
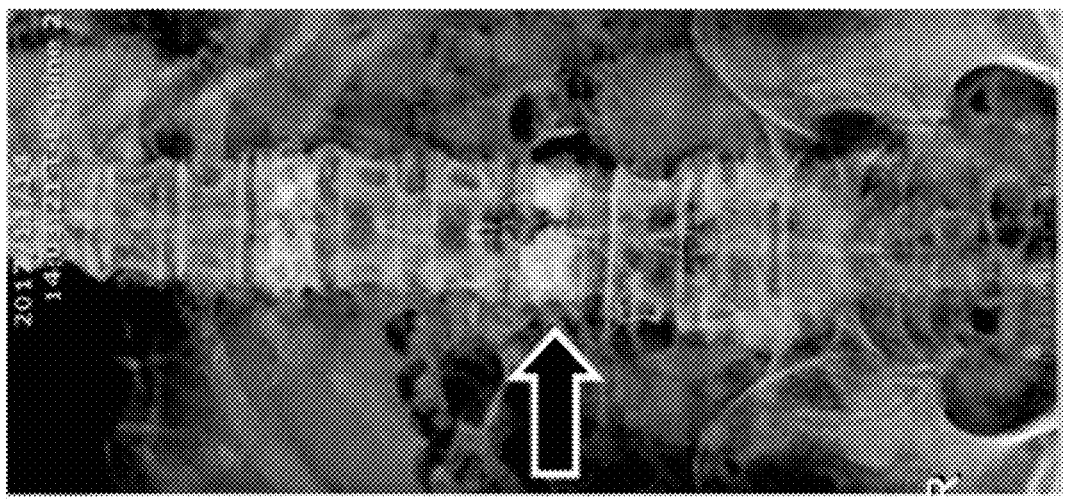
FIG. 9A-9C are X-ray images of the present invention.
Figure 9B:
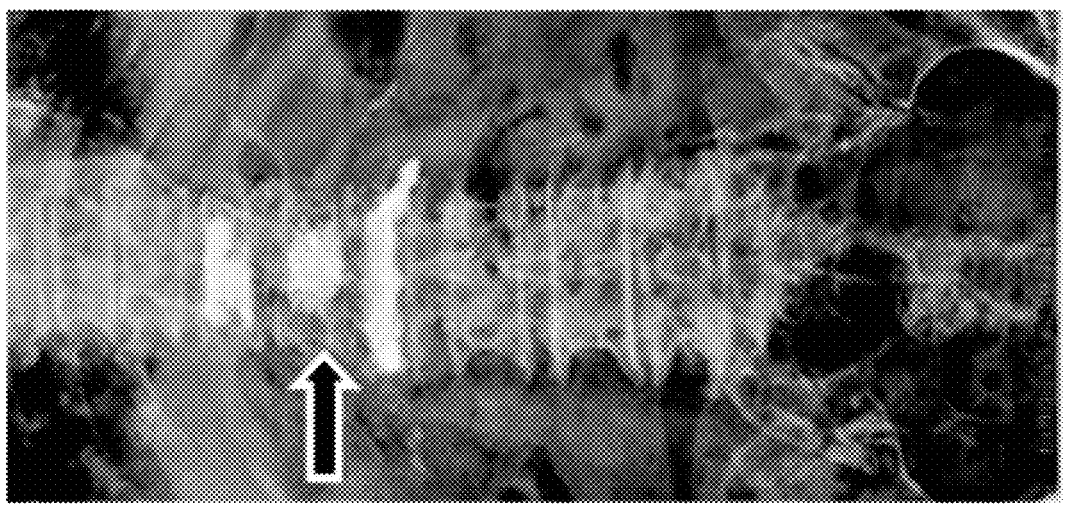
Figure 9A:
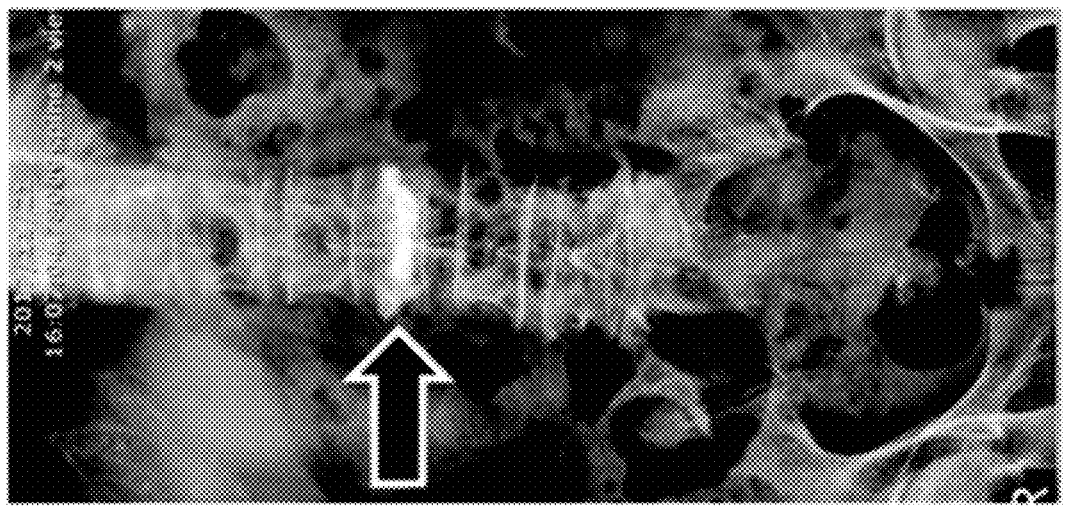

The evaluation principle of evaluating the bone cement injection results is shown in FIG. 8 and FIG. 9A-9C, the schematic and X-ray images of the bone cement injection cases. As shown in FIG. 8, the "excellent" distribution of bone cement injection is a condition that the bone cement can be completely guided to the opposite side of the vertebral body and evenly distributed; the "good" distribution of bone cement injection is a condition that the bone cement can be guided by the negative pressure to cross the midline of the vertebral body and evenly distributed; the "poor" distribution of bone cement injection is a condition that the bone cement guided by the negative pressure cannot cross the midline of the vertebral body; and the "failed" distribution of bone cement injection is a condition that the bone cement was limited to the injection area. For FIG. 9A-9C, the FIG. 9A is the X-ray image of the "excellent" bone cement injection result, FIG. 9B is the X-ray image of the "good" bone cement injection result and FIG. 9C is the X-ray image of the "poor" bone cement injection result.

The statistical result of the 256 cases of 159 patients is shown in FIG. 10. The groups with two-way bone cement injection with negative pressure guidance (Condition 5 & 6) has much more cases ranked as "excellent" than the groups with two-way bone cement injection (Condition 3 & 4) and the groups with one-way bone cement injection (Condition 1 & 2), and only has a percentage of the single digits in all cases ranked as "poor" or "failed" which is far lower than other groups. In the case of cement leakage, Condition 5 & 6 also only has a percentage of the single digits which is still lower than other groups. It is obvious that the negative pressure guided bone cement injection system with sensing device disposed on the negative pressure system and/or the pushing system can observe the influencing factors of the bone cement injection (such as the negative pressure value of the end of the negative pressure needle tube of the embodiment) and send the sensing results to the control system for control and adjust the bone cement injection (the positive pressure value of the end of the cement injection). It can provide a better bone cement injection efficiency and bone cement filling effect, and effectively avoid the leakage of bone cement during the cement injection process.

The invention claimed is:

1. A negative pressure guided bone cement injection system comprising:
a negative pressure system comprising:
a negative pressure introduction device; wherein the negative pressure introduction device comprises a cavity, a side connected to an aspiration source, and a first opening on an opposite side; wherein the aspiration source is for introducing a negative pressure and the first opening is for outputting the negative pressure;
a pushing system comprising a pushing pump and a bone cement implantation system, wherein the pushing pump is connected to the bone cement implantation system for pushing a bone cement material in the bone cement implantation system for delivery;
a controller connected to the negative pressure system and the pushing system; and
at least one sensor electrically connected to the negative pressure system and the controller for sensing at least one environmental parameter and sending the at least one environmental parameter to the controller;
wherein the at least one sensor includes a pressure sensor; wherein when the negative pressure guided bone cement injection system is turned on, the aspiration source starts to operate, and the pressure sensor measures an initial negative pressure value; wherein the controller compares the initial negative pressure value or a dynamic negative pressure value measured by the pressure sensor with a preset threshold; wherein the controller starts to drive the pushing pump for bone cement injection when the dynamic negative pressure value is lower than the preset threshold; wherein the bone cement injection stops when the dynamic negative pressure value exceeds a target value.

2. The system of claim 1, wherein the negative pressure system further comprises a first adjuster connected to the aspiration source for adjusting a strength of the negative pressure of the aspiration source and electrically connected to the controller for adjusting the aspiration source by control of the controller.

3. The system of claim 2, wherein the aspiration source is a negative pressure pump or a medical negative pressure socket.

4. The system of claim 2, wherein the first adjuster is a flow regulating valve, a current regulator or a voltage regulator.

5. The system of claim 1, wherein the pushing system further comprises a second adjuster electrically connected to the pushing pump and the controller, the second adjuster configured for being controlled by the controller and adjusting the pushing strength of the pushing pump on the bone cement material.

6. The system of claim 5, wherein the second adjuster is a flow regulating valve, a current regulator or a voltage regulator.

7. The system of claim 1, wherein the at least one sensor is further disposed on the negative pressure system and the pushing system for sensing the at least one environmental parameter of the negative pressure system and the pushing system and sending the at least one environmental parameter to the controller to adjust and control the negative pressure system and the pushing system.

8. The system of claim 1 or 7, wherein the at least one environmental parameter is a viscosity of the bone cement material, a flow rate of the bone cement, a density of the bone cement material, a bone density, a negative pressure in the negative pressure introduction device, a negative pressure in the negative pressure system or a negative pressure in a target region.

9. The system of claim 1 or 7, wherein the at least one sensor senses the at least one environmental parameter and sends the at least one environmental parameter to the controller for calculating and generating an operation result that is considered by the controller for adjusting a strength of the negative pressure of the negative pressure system and/or the pumping strength of the pumping system.

10. The system of claim 1, wherein the pumping system comprises a mixer adjusting a ratio of a plurality of the bone cement materials and then mixing the materials, and the mixer electrically connected to the controller which adjusts the ratio of the bone cement materials to control a fluidity of the bone cement material which is delivered through the bone cement implantation system.

11. The system of claim 10, wherein the bone cement materials that adjusted by the mixer are selected from N, N-dimethyl-p-toluidine, hydroquinone, methyl methacrylate, calcium phosphate, calcium sulfate derivative, calcium oxide, calcium carbonate, calcium hydroxide, calcium magnesium phosphate, hydroxyapatite, calcium hydroxyapatite, calcium dihydrogen phosphate, calcium metaphosphate, phosphate derivative, dihydrate Calcium hydrogen phosphate, tricalcium phosphate, lactone polymer, amino acid polymer, anhydride polymer, orthoester polymer, acid anhydride imine copolymer, orthocarbonate polymer, polyhydroxyalkanoate, dioxane Hexone polymer, phosphate polymer, polylactic acid, mixed polylactic acid, polyglycolic acid, polylactic acid-glycolic acid, poly(L-lactic acid-lactic acid) copolymer, polylactic acid-polytrimethylene carbonate) Copolymer, polyhydroxybutyrate, polycaprolactone, polyvalerolactone, polybutyrolactone, polyacrylic acid, polycarboxylic acid, polyallylamine hydrochloride, polydiallyldimethyl chloride Ammonium, polyethyleneimine, polypropylene fumarate, polyvinyl alcohol, polyvinylpyrrolidone, polyethylene, polymethylester, carbon fiber, polyethylene glycol, polyethylene oxide, poly(2-ethyl-2-oxazole Porphyrin), polyethylene oxide polypropylene oxide block copolymer, polyethylene terephthalate polyamine, any one thereof or any combination thereof.

12. The system of claim 1, wherein the negative pressure introduction device is a first needle tube comprising a first needle body and a first tube body connected to the first needle body, wherein the first needle body has the opposite side with the first opening; wherein the bone cement implantation system is a second needle tube comprising a second needle body and a second tube body connected to the second needle body, wherein the second needle body has a second opening.

13. The system of claim 12, further comprising at least one set of trocars comprising:
   a first trocar comprises at least one first connecting portion, wherein the first trocar is sleeved on the first needle tube and an extending direction of the at least one first connecting portion forms a first indication angle with an opening direction of the first opening;
   a second trocar comprises at least one second connecting portion, wherein the second trocar is sleeved on the second needle tube and an extending direction of the at least one second connecting portion forms a second indication angle with an opening direction of the second opening; and
   at least one connector connected to the at least one first connecting portion and the at least one second connecting portion to restrict and fix the positions of the first needle tube and the second needle tube, and the first opening is adjusted to be disposed face to face with the second opening based on the first indication angle and the second indication angle.

14. The system of claim 13, wherein the first opening and the second opening are an opening on one side or an opening on a bottom of a bent needle body.

15. The system of claim 13, wherein the connector is integrally formed, sleeved on, or screwed with the at least one first connecting portion and the at least one second connecting portion.

* * * * *